United States Patent [19]

Menger

[11] Patent Number: 4,791,927
[45] Date of Patent: Dec. 20, 1988

[54] DUAL-WAVELENGTH LASER SCALPEL BACKGROUND OF THE INVENTION

[75] Inventor: Eva L. Menger, Madison, N.J.

[73] Assignee: Allied Corporation, Morris Township, Morris County, N.J.

[21] Appl. No.: 68,688

[22] Filed: Jul. 1, 1987

Related U.S. Application Data

[63] Continuation-in-part of Ser. No. 813,751, Dec. 26, 1985, abandoned.

[51] Int. Cl.$^4$ ............................................. A61B 17/36
[52] U.S. Cl. ................................................. 128/303.1
[58] Field of Search ................. 128/303.1, 395–398; 219/121 L; 307/425, 426; 372/41

[56] References Cited

U.S. PATENT DOCUMENTS 4,272,733 6/1981 Walling et al. ........................ 373/41
4,280,109 7/1981 Stappaerts .......................... 307/425
4,499,897 2/1985 Roussel ................................ 128/395

FOREIGN PATENT DOCUMENTS 214292 10/1984 Fed. Rep. of Germany ... 128/303.1
215698 11/1984 Fed. Rep. of Germany ... 128/303.1

OTHER PUBLICATIONS

"lasers Cut a Swath in Surgical and Medical Applications" Jako IEEE, July 1985

Primary Examiner—Max Hindenburg
Attorney, Agent, or Firm—Anibal Jose Cortina; Gerhard H. Fuchs

[57] ABSTRACT

A medical laser provides to a biological target both a laser wavelength in the deep red-near infrared region of the spectrum and a wavelength in the blue-near ultraviolet region. The short wavelength blue light cuts the target tissue, while the longer-wavelength red light cauterizes. The long-wavelength radiation may be provided by an alexandrite laser, with a harmonic generator providing half the fundamental wavelength. Alternatively, the short-wavelength radiation may be provided by an alexandrite laser, with a harmonic generator providing half the fundamental wavelength. Alternatively, the short-wavelength radiation may be provided by a xenon fluoride laser, with a Raman cell shifting the radiation from the ultraviolet into the visible. Generally, at least one of the wavelengths is visible on the target and both wavelengths may readily be transmitted by conventional optical fibers.

20 Claims, 1 Drawing Sheet

DUAL-WAVELENGTH LASER SCALPEL
BACKGROUND OF THE INVENTION

CROSS-REFERENCE TO RELATED APPLICATIONS

This application is a continuation-in-part of copending application Ser. No. 813,751, which was filed Dec. 26, 1985, now abandoned, and whose disclosure is specifically incorporated by reference herein.

DESCRIPTION
BACKGROUND OF THE INVENTION

1. Field of the Invention

This invention relates to a medical laser; more particularly, to a single laser that provides radiation of two wavelengths, one for cutting biological tissue and the other for cauterizing.

2. Description of the Prior Art

In the past, lasers have been in use as a surgical scalpel, wherein the predominant effects on biological tissue have been thought to be thermal. The laser scalpel can either stem blood flow through photocoagulation or incise tissue through photoablation. Photocoagulation occurs when light absorption produces a temperature rise high enough to denature proteins in the target tissue, a process chemically similar to frying an egg. In the retina, a 10°–20° C. temperature rise will cause photocoagulation; laser photocoagulation is used to sear closed small abnormal blood vessels, such as often form in the retina of diabetics. In the prior art, cutting or photovaporization occurs when light energy is deposited in the tissue, at a rate sufficient to heat the water in the tissue to boiling substantially instantaneously to thereby ablate the tissue.

The laser of choice for a given procedure is dictated by the laser's characteristics as well as the optical properties of the target tissue. Scattering conducts light away from the site of its placement and ultimately results in heating of the adjoining tissue. This can be desirable or undesirable, depending upon the intent of the laser intervention. If the light is at a wavelength that is not strongly absorbed, it penetrates deeply and undergoes extensive scattering, resulting in diffuse heating. This is the case for Nd:YAG (YAG) and argon ion lasers; both are well suited for inducing photocoagulation. If the wavelength is strongly absorbed, there is a rapid rise in temperature at the site where the light strikes and little light penetration or scattering occurs. This results in a well-defined region of photoablation with little lateral spread of heat damage, which is desirable for incisions. $CO_2$ lasers fall in this category and are used for incision. The $CO_2$ laser radiation at 10.6 $\mu$m is absorbed by water.

Cutting and cauterizing are not quite the dichotomous operations presented above. In many procedures one needs to do both simultaneously. This can be accomplished, albeit not optimally, with a laser operating at a single wavelength, by varying the focal point size and power of laser output. Thus, in using a $CO_2$ laser to seal a blood vessel, a surgeon may defocus the beam and lower the power. For small vessels, at least, the resulting "edema cuff" may be enough to stop the bleeding. Similarly, in using a YAG laser to cut, a surgeon may focus tightly and increase the laser power. While incisions can be made in that way, there are thermal effects beyond the impact site. While there is essentially no rise in temperature surrounding a $CO_2$ laser-induced incision, millimeters away from a YAG cut tissue temperature rises to over 200° F. This is obviously undesirable, particularly in surgery on delicate tissue, such as the brain or spinal column.

Since optimal cutting and optimal coagulating are not achieved at the same wavelength, multilaser systems have been proposed by Jako. Up to now cutting has been performed with wavelengths in the far infrared range with coagulating being done with wavelengths in the near infrared or visible range. These systems can deliver a beam from a $CO_2$ laser, a YAG laser or both (IEEE Spectrum, March, 1985). However, multilaser systems are inherently complex and costly. Further, both lasers deliver light in the infrared wavelength range, $CO_2$ at 10.6 $\mu$m and ND:YAG at 1.06 $\mu$m and, as a result the beams cannot be seen. Moreover, the $CO_2$ laser cannot be used with fiber optics and is thus not suitable for endoscopic cutting applications.

Wengler et al., in German Patent Application No. DD 217 711A, disclosed a surgical laser device that consists of a YAG laser in combination with a second harmonic generating (SHG) crystal. The output of the laser is at 1060 nm in the infrared and is not visible. The SHG crystal can be pivoted into the laser beam path to provide a visible beam for target location, however the second harmonic wavelength at 530 nm cannot cut.

A mechanical device that provides simultaneous cutting and cauterizing was disclosed in U.S. Pat. No. 4,534,347, issued Aug. 13, 1985. The device incorporates in a conventional surgical blade a microwave antenna that emits microwave energy to heat water molecules in tissue cells and cauterize blood at the same time an incision is made.

SUMMARY OF THE INVENTION

In accordance with the present invention, a dual-wavelength laser system for cutting and coagulating tissue is provided. The laser comprises, in combination, (a) a source of a beam of coherent radiation having a first wavelength in the range between about 500 and about 800, preferably 600–700 nm, (b) means for doubling at least a part of the coherent radiation beam to a second wavelength in the range between about 250 and about 400, preferably 300–350 nm, and (c) beam delivery means for directing the beams of coherent radiation onto a target. In an alternative embodiment, the fundamental wavelength is in the range between about 250 and about 350, preferably 300–350 nm, and the second wavelength is longer than about 600 nm. In this case wavelength shifting is performed, for example, by Raman shifting.

In essence, the invention in part resides in the unexpected discovery that cutting can be performed with light in the near ultraviolet end of the spectrum. Thus, the use of a laser which is a single unit having a fundamental wavelength emission of about 500–800 nm which can be doubled into the ultraviolet range of about 250–350, preferably 300–350 nm is for the first time proposed for surgical applications. In this case the fundamental serves to cauterize and the doubled emission serves to cut. The cutting is achieved not because the water absorbs the light and heats to boiling as in the case with prior infrared systems, but because proteins and other components in the tissue readily absorb the doubled emission in the near ultraviolet and photoablate in a localized manner.

Examples of single solid state laser media which can be used for this embodiment include: Cr:BeAl$_2$O$_4$ (Alexandrite) with a fundamental tunable wavelength range of about 701 nm–818 nm; Ti:Al$_2$O$_3$ (titanium doped sapphire) with a tunable range of about 680 nm–1000 nm; Cr:Al$_2$O$_3$ (ruby) with a wavelength of about 694–890 nm; Cr:Be$_3$Al$_2$(SiO$_3$)$_6$ (emerald) with a tunable range of about 790–890 nm; Cr:Gd$_3$Sc$_2$Ga$_3$O$_{12}$ (chromium doped GSGG) with a tunable range of about 742–842 nm; Ti:BeAl$_2$O$_4$ (titanium doped chrysoberyl) with a tunable range of about 700–1100 nm; Nd:Cr:Gd$_3$Sc$_2$Ga$_3$O$_{12}$ (neodynium/chromium doped 6566) with a wavelength of about 1064 nm; Cr:SrAlF$_5$ (chromium doped strontium aluminum fluoride) with a tunable wavelength of about 850 nm–1050 nm and Cr:KZnF$_3$ (chromium doped potassium zinc flouride) with a tunable wavelength of about 785 nm–865 nm.

In an alternative construction the single source laser medium will be one with a fundamental ultraviolet wavelength for cutting which is shiftable for coagulating into the visible range, for example, by Raman shifting. Examples include, among others, xenon flouride, xenon chloride and nitrogen lasers.

In both cases the coagulating wavelength is visible and the ultraviolet in the near range causes tissue to luminesce, as contrasted with infrared, so in use a separate visible probe laser is never necessary.

A further advantage of the invention is that with a single beam, both coagulating and cutting light can be delivered at a single site without complicated optics, for example, by doubling the center of the beam and leaving the donut shaped outer portion at the fundamental, and thus cutting and causing immediate cauterization at the same time. Further, by staying in the near ultraviolet range where DNA does not absorb, genetic damage is likely to be avoided. Other advantages result, for example, in cancer surgery when cutting and cauterizing are performed simultaneously, with the invention, the spread of cancerous cells is prevented and surgically induced metastasis avoided.

The single laser system is simpler and less expensive than are multilaser systems for cutting and cauterizing. Both wavelengths of radiation are readily transmitted by convention fiberoptic cable. The capability of using the system of the invention in optical fibers is especially important, for example, in endoscopic applications. More specifically, in an endoscopic environment major surgical intervention need not be performed, for example, in the gastro intestinal tract since a large number of conditions previously only treated by major surgical intervention can now be treated by endoscopic laser surgery. By delivering the light through a flexible optical fiber major incision of the abdominal cavity and elsewhere is thus avoided. Further, generally at least one of the wavelengths of light is visible; thus, there is no need to provide a third light beam specifically for visualization.

DETAILED DESCRIPTION OF THE INVENTION

Figure 1:
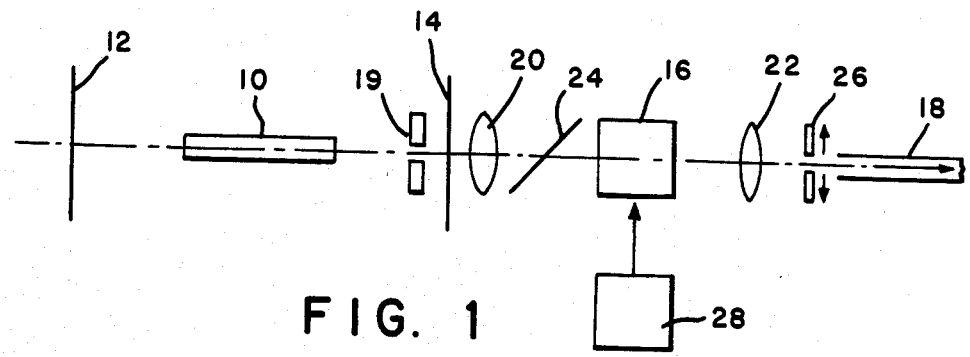
FIG. 1 is a schematic drawing of a laser system of the present invention.

Over the past 20 years, a great deal, of research has been done in the area of laser surgery, and many review articles have appeared—see, e.g., J. A. Dixon, Proc. of the IEEE 70, 579 (1982) and G. J. Jako, IEEE Spectrum, March, 1985, pp. 82–87. Lasers have been used in surgery both to cut and to cauterize; i.e., coagulate the blood to stop or prevent bleeding. These lasers in both cases, have operated in the infrared range, with cutting in the far infrared with coagulation in the near infrared. Some coagulation has been achieved in the the past with the visible, e.g., blue-green, with an argon laser.

It is desirable in many surgical applications to have a scalpel which both cuts and cauterizes simultaneously. Such a scalpel would be particularly useful in surgery of highly vascular tissue such as the liver, or in procedures that typically involve large incisions, as in plastic surgery or orthopedic procedures. Reduced bleeding during surgery would both provide the surgeon with a better field of view and cause less blood loss for the patient. In cases of tumor removal, sealing off the blood and lymph vessels may reduce or eliminate the incidence of surgically induced metastases.

The present device provides laser radiation to both cut and cauterize. More specifically, it has been discovered, as discussed above, that cutting can be achieved in the near ultraviolet range because proteins absorb in this range and substitute more effectively for the previously discussed infrared boiling of water in tissue to cut. Two different wavelengths of light are used simultaneously; one wavelength is chosen primarily for its ability to cut, i.e. the near ultraviolet; the other, e.g., the visible to cauterize. It is a straightforward task to vary the relative intensities of the two wavelengths to optimize the cut/sear ratio for different procedures and different tissue.

In a preferred embodiment, the two different wavelengths are obtained from one laser by using both the fundamental wavelength—at least above 500 nm and preferably between about 500 and 800 nm most preferably 600–700 nm—and the second harmonic, produced by frequency-doubling the fundamental to 250–400 nm, most preferably 300–350 nm. Both wavelengths are readily transmitted through flexible quartz fiber optics. Thus, endoscopic use is possible as contrasted to CO$_2$ lasers. The fundamental cauterizes and the shifted wavelength cuts. When the latter wavelength is in the violet or blue region of the spectrum, it has the additional advantage of being readily visible on red tissue.

In another embodiment, the fundamental wavelength is in the range between about 300 and about 400 nm and the shifted wavelength is longer than about 600 nm. In that case, the fundamental cuts and the shifted wavelength cauterizes; generally, either or both wavelengths are visible, or if not visible, the cutting is near enough to visible to cause tissue to luminesce when being cut so that a separate visible probe beam is not necessary.

There are a variety of lasers that provide output radiation in the range discussed above, with some being tunable over a generally broader range than that set forth. Among these are various dye lasers and solid state lasers, such as alexandrite; BEL:Nd; GSGG:Cr; GSGG:Nd,Cr; ruby; as well as others previously listed. Solid state lasers are preferred, because they are simpler in construction, capable of high power operation, and easier to work with. Each of the solid state lasers listed emits in the desired range; the Cr-doped lasers emit near the lower end of the desired wavelength range and would incorporate means for frequency-doubling. Alexandrite, ruby, sapphire, emerald and scandium borate are preferred, because they are available commercially. Alexandrite is particularly preferred, because it is tunable and it provides a visible indication of beam position. Preferably, the material used is continuously tunable.

Lasers that are suitable for the embodiment in which the fundamental wavelength cuts include xenon fluoride, xenon chloride, and nitrogen.

A laser of the present invention is depicted schematically in FIG. 1. The laser comprises laser medium 10 in a resonant cavity defined by mirrors 12 and 14, at least one of which (here depicted as 14) is partly reflecting. When medium 10 is excited by a conventional (pulsed or cw) pump source (not shown), coherent radiation is emitted through mirror 14 and passes through beam shifting means 16. Thereafter, the beam, including both the fundamental and the harmonic wavelengths, passes to the target (not shown) through beam delivery means 18, which may, for example, be a fiberoptic cable. FIG. 1 also depicts optional aperture 19; optional lenses 20 and 22, which can, for example, provide a collimated beam to beam delivery means 18; optional tuning element 24 (which may be used if the laser is tunable); and optional intensity controller 26.

Optional lens 20 may focus the beam into the beam shifting means 16 or, alternatively, it may cause the beam entering the beam shifting means to diverge, thereby causing the central portion of the beam to be wavelength-shifted and the off-axis portion to remain at the fundamental wavelength.

Tuning element 24 may be any conventional tuning means, such as a prism, optical grating, birefringent filter, etc.

Beam shifting means 16 may be a non-linear crystal that doubles the frequency of the beam incident upon it (i.e., a second harmonic generator). Alternatively, by mixing the fundamental and doubled frequencies, the frequency may be tripled. These harmonic generators (doublers, triplers, etc.) are available commercially; for example, from Lasermetrics, Englewood, N.J. Optional controller 28 may be pulsed to provide alternating shifted and unshifted radiation.

In the embodiment where the fundamental wavelength is shifted to longer wavelengths, beam shifting means 16 may be a Raman cell filled with a suitable Raman active gas or liquid. In addition to shifting the wavelength, a Raman cell can improve the transverse mode structure of the beam. A hydrogen gas Raman cell is preferred, because it shifts the wavelength by the greatest amount per Stokes transition. Controller 28 would not be used with a Raman cell.

Figure 2:
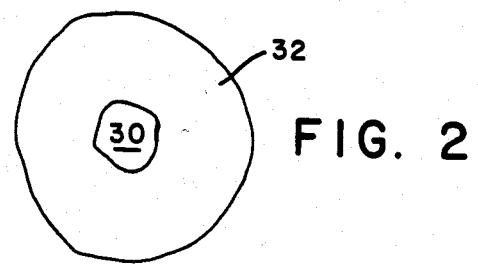
FIG. 2 is a cross section through a laser beam as it is incident on a target.

Optional lens 22 may be selected to intentionally introduce chromatic aberration, so that the fundamental and shifted wavelengths are not focused at the same point. In that way, for example, a focused shorter-wavelength beam can provide cutting at the target, while the unfocused, longer-wavelength beam cauterizes in the surrounding region. A cross section through the resulting beam at the target is shown schematically in FIG. 2, where 30 is the short-wavelength beam and 32 the surrounding long-wavelength beam.

Optional intensity control 26 can comprise one or more irises, filters, etc. to control the intensities, and/or relative intensities, of the fundamental and shifted radiation.

Figure 3:
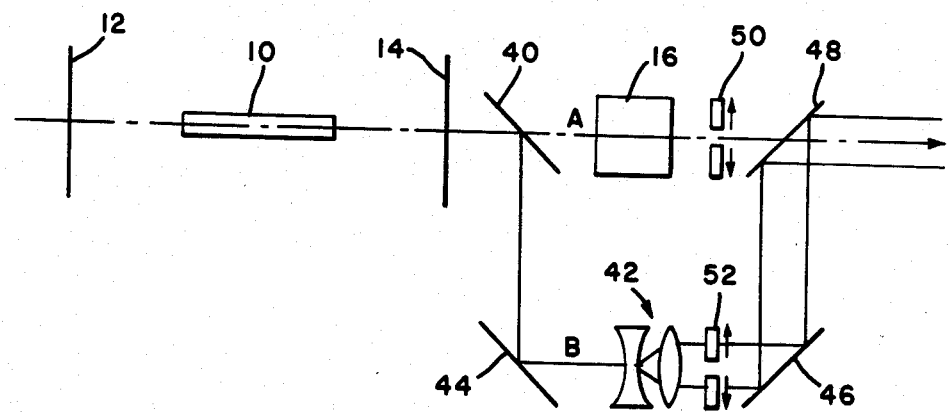
FIG. 3 is a schematic drawing of another embodiment of a laser system of the present invention.

FIG. 3 depicts an embodiment in which partially-reflecting mirror 40 divides the beam into two parts, one of which (beam A) is shifted, while beam B is expanded by beam expander 42. Mirrors 44 and 46 and partially-transmitting mirror 48 cause the two beams to pass to the target coaxially. Independently controlling the intensities of the fundamental and shifted radiation is readily accomplished by controlling the beam-splitting ratio of partially-reflecting mirror 40 and/or by using optional intensity control means 50 and 52. In the embodiment where the fundamental wavelength is shorter, the shifted beam is expanded. In any case, the appearance of the resultant beam on the target is shown in cross section in FIG. 2.

The following examples are presented in order to provide a more complete understanding of the invention. The specific techniques, conditions, materials, and results set forth to illustrate the principles and practice of the invention are examplary and should not be construed as limiting the scope of the invention.

EXAMPLE 1

A Q-switched alexandrite laser emitting at 750 nm, with pulse energy of 2J, was frequency-doubled to produce pulses at 375 nm with energy in excess of 250 mJ. A filter reduced the intensity of the fundamental beam by a factor of 50-100. The laser was run at 100 Hz. The beam, comprised of both wavelengths, was focused to a spot of about 1 nm in diameter and directed at body tissue. The combined effect of the two wavelengths was observed, with the UV beam inducing incision and the fundamental beam inducing photocoagulation. The flow of blood was inhibited during the incision by the searing closed of blood vessels. This resulted in a clearer field of view for the surgeon and reduced blood loss for the patient. In the case of tumor resection, the fact that the blood vessels and lymph vessels were photocoagulated during the incision greatly reduced the probability of surgically-induced metastasis.

EXAMPLE 2

A 0.125 J xenon fluoride laser is run at 200 Hz, producing 10 ns pulses of 350 nm radiation. The output is focused into a ½ m cell filled with hydrogen gas at 10 atmospheres. The third Stokes transition of the hydrogen shifts the light by 12,465 cm$^{-1}$ with about 10% efficiency, thus producing radiation at 621 nm. The 350 nm fundamental is used with the 621 nm radiation as described in Example 1.

We claim:

1. A dual-wavelength laser system for both cutting and coagulating tissue, comprising, in combination:
   (a) a single source of a beam of coherent radiation having a first wavelength, which wavelength is such that a beam of coherent radiation from said single source is effective for cauterizing bleeding blood vessels through photocoagulation, and said single source being selected from the group of lasers having a fundamental wavelength of 500-800 nm.
   (b) means for selectively doubling the wavelength of the beam of coherent radiation from said single source to a second wavelength beam of coherent radiation, said second wavelength being in the range of 250-400 nm such that the beam is effective for cutting tissue by photoablation with little light penetration or scattering and consequently little lateral spread of heat damage; and (c) beam delivery means for directing at least one of the respectively selected said beams of coherent radiation onto a target.

2. The system of claim 1 in which the source of coherent radiation is an alexandrite laser.

3. The system of claim 2 in which the doubling means is a frequency doubler.

4. The system of claim 1 in which the source of coherent radiation is a ruby laser.

5. The system of claim 4 in which the doubling means is a frequency doubler.

6. The system of claim 1 in which the beam incident on the doubling means is divergent, whereby only the central portion of the beam is doubling.

7. The system of claim 1 in which the beam delivery means introduces chromatic aberration, whereby the first and second wavelength beams are not focused at the same point.

8. The system of claim 1 in which the beam delivery means includes means for expanding the first wavelength beam relative to the second.

9. The system of claim 1 further comprising means for pulsing the means for selectively doubling the wavelength on and off to alternate the arrival at the target of the first and second wavelength beams.

10. The system of claim 1 further comprising means for controlling the intensities of the two radiation beams.

11. The system of claim 1 wherein said means for selectively doubling is arranged for doubling said first wavelength to a range of 300–350 nm with said laser medium being a fundamental wavelength of 600–700 nm.

12. The system of claim 1 wherein said single source comprises a laser medium selected from the group consisting essentially of $Cr:BeAl_2O_4$, $Ti:Al_2O_3$, $Cr:Al_2O_3$, $CrBe_3Al_2(SiO_3)_6$, $Cr:Gd_3Sc_2Ga_3O_{12}$, $Ti:BeAl_2O_4$, $Nd:Cr:Gd_3Sc_2Ga_3O_{12}$, $Cr:SrAlF_5$ and $Cr:KZnF_3$.

13. The system of claim 1 wherein said laser medium is $Cr:BeAl_2O_4$ (Alexandrite).

14. A dual-wavelength laser system for cutting and coagulating tissue comprising, in combination, (a) a source of a beam of coherent radiation having a first wavelength in the range between about 300 nm and about 400 nm, (b) means for shifting at least a part of the coherent radiation beam to a second wavelength longer than about 600 nm, and (c) beam delivery means for directing the beams of coherent radiation onto a target.

15. The system of claim 14 in which the source of coherent radiation is a xenon fluoride laser.

16. The system of claim 14 in which the shifting means is a Raman cell.

17. The system of claim 16 in which the Raman cell is filled with hydrogen.

18. The system of claim 14 in which the beam delivery means introduces chromatic aberration, whereby the first and second wavelength beams are not focused at the same point.

19. The system of claim 14 in which the beam delivery means includes means for expanding the second wavelength beam relative to the first.

20. The system of claim 14 further comprising means for controlling the intensities of the two radiation beams.

* * * * *

UNITED STATES PATENT AND TRADEMARK OFFICE
CERTIFICATE OF CORRECTION

PATENT NO. : 4,791,927
DATED : December 20, 1988
INVENTOR(S) : Eva L. Menger

It is certified that error appears in the above-identified patent and that said Letters Patent is hereby corrected as shown below:

Cover Page, Title reads: "DUAL-WAVELENGTH LASER SCALPEL
BACKGROUND OF THE INVENTION"

Should read -- DUAL-WAVELENGTH LASER SCALPEL --.

Col. 8, line 8: "claim 1" should read -- claim 12 --.

Signed and Sealed this

Fifth Day of September, 1989

Attest:

DONALD J. QUIGG

Attesting Officer

Commissioner of Patents and Trademarks